US012778556B2

(12) United States Patent
Veronesi

(10) Patent No.: US 12,778,556 B2
(45) Date of Patent: Nov. 3, 2026

(54) ULTRASOUND SYSTEM FOR AUTOMATIC SPECTRAL DOPPLER ULTRASOUND DATA ACQUSITION

(71) Applicant: GE Precision Healthcare LLC, Waukesha, WI (US)

(72) Inventor: Federico Veronesi, San Lazzaro di Savena (IT)

(73) Assignee: GE Precision Helthcare LLC, Waukesha, WI (US)

( * ) Notice: Subject to any disclaimer, the term of this patent is extended or adjusted under 35 U.S.C. 154(b) by 0 days.

(21) Appl. No.: 19/058,272

(22) Filed: Feb. 20, 2025

(65) Prior Publication Data

US 2026/0240526 A1 Aug. 20, 2026

(51) Int. Cl.
*A61B 8/00* (2006.01)
*A61B 8/06* (2006.01)

(52) U.S. Cl.
CPC ................ *A61B 8/488* (2013.01); *A61B 8/06* (2013.01); *A61B 8/4444* (2013.01); *A61B 8/461* (2013.01); *A61B 8/469* (2013.01); *A61B 8/54* (2013.01)

(58) Field of Classification Search
CPC ......... A61B 8/488; A61B 8/06; A61B 8/4444; A61B 8/461; A61B 8/469; A61B 8/54
See application file for complete search history.

(56) References Cited

U.S. PATENT DOCUMENTS

| | | | | |
|---|---|---|---|---|
| 5,562,097 | A | 10/1996 | Yao | |
| 6,241,675 | B1 * | 6/2001 | Smith | G01S 15/8993 600/443 |
| 6,322,509 | B1 | 11/2001 | Pan et al. | |
| 6,423,006 | B1 | 7/2002 | Banjanin | |
| 6,464,641 | B1 | 10/2002 | Pan et al. | |
| 9,579,083 | B2 | 2/2017 | Guracar | |
| 10,806,433 | B2 | 10/2020 | Lee et al. | |
| 11,160,536 | B2 | 11/2021 | Faraggi | |
| 2003/0109785 | A1 | 6/2003 | Buck et al. | |
| 2007/0255136 | A1 * | 11/2007 | Kristofferson | G01S 7/52073 600/437 |
| 2014/0018680 | A1 * | 1/2014 | Guracar | A61B 8/5276 600/440 |
| 2015/0115773 | A1 * | 4/2015 | Li | A61B 8/12 29/25.35 |

(Continued)

FOREIGN PATENT DOCUMENTS

| | | | |
|---|---|---|---|
| JP | 6829656 | B2 | 2/2021 |
| WO | 2008/101684 | A1 | 8/2008 |

*Primary Examiner* — Sean A Frith
(74) *Attorney, Agent, or Firm* — SPQ IP LLC

(57) ABSTRACT

An ultrasound system is provided for automatic spectral Doppler ultrasound data acquisition. The ultrasound system may acquire 4D color flow ultrasound data of an ROI of a subject. The ultrasound system may display a 4D color flow ultrasound image of the ROI of the subject based on the 4D color flow ultrasound data. The ultrasound system may receive a user input selecting a measurement location in the 4D color flow ultrasound image of the ROI of the subject. The ultrasound system may automatically acquire spectral Doppler ultrasound data corresponding to the measurement location based on the user input. The ultrasound system may display spectral Doppler information corresponding to the spectral Doppler ultrasound data.

20 Claims, 11 Drawing Sheets

(56) References Cited

U.S. PATENT DOCUMENTS

| | | | | |
|---|---|---|---|---|
| 2015/0223781 | A1* | 8/2015 | Abe | A61B 8/466 600/437 |
| 2015/0359506 | A1* | 12/2015 | Takimoto | A61B 5/318 600/441 |
| 2016/0095573 | A1* | 4/2016 | Tanaka | A61B 8/5207 600/443 |
| 2017/0086789 | A1* | 3/2017 | Brandl | G16H 50/30 |
| 2019/0254630 | A1* | 8/2019 | Vignon | G01S 7/52071 |
| 2020/0229795 | A1 | 7/2020 | Tadross et al. | |
| 2021/0077065 | A1 | 3/2021 | Pernot et al. | |
| 2021/0153846 | A1 | 5/2021 | Bellamkonda et al. | |
| 2022/0061810 | A1 | 3/2022 | Dickie et al. | |
| 2023/0143880 | A1 | 5/2023 | Jago et al. | |
| 2023/0200784 | A1 | 6/2023 | Kobayashi et al. | |
| 2023/0285005 | A1 | 9/2023 | Ayinde et al. | |

* cited by examiner

ULTRASOUND SYSTEM FOR AUTOMATIC SPECTRAL DOPPLER ULTRASOUND DATA ACQUSITION

TECHNICAL FIELD

The present disclosure relates to an ultrasound system for automatic spectral Doppler ultrasound data acquisition. More specifically, the present disclosure relates to an ultrasound system that acquires four-dimensional (4D) color flow ultrasound data of a region of interest (ROI) of a subject, displays a 4D color flow ultrasound image of the ROI of the subject based on the 4D color flow ultrasound data, receives a user input selecting a measurement location in the 4D color flow ultrasound image of the ROI of the subject, and automatically performs spectral Doppler ultrasound data acquisition using the measurement location.

BACKGROUND

Mitral valve regurgitation is a common type of heart valve disease that affects a large number of patients. During mitral valve regurgitation, the mitral valve does not fully close during systole, which results in the backwards flow of blood from the left ventricle to the left atrium. Regurgitant volume may refer to the amount of blood that flows backwards through the mitral valve during a cardiac cycle. A mitral regurgitation jet may refer to a high-velocity jet that may be detected in the left atrium during systole. The *vena contracta* may refer to a point in a mitral regurgitation jet having a minimum diameter and a maximum fluid velocity. By measuring a diameter of the *vena contracta*, a clinician may estimate the severity of mitral regurgitation and assess the regurgitant volume.

Echocardiography is a procedure that permits the assessment of mitral regurgitation and the determination of a regurgitant volume. For example, an ultrasound system may acquire color flow ultrasound data of a heart of a subject, and display color flow ultrasound images that visualize fluid flow through the mitral valve of the subject. Restated, the color flow ultrasound images may depict a mitral regurgitation jet. Further, in some cases, the ultrasound system may acquire spectral Doppler ultrasound data of the mitral regurgitant jet, and display spectral Doppler information that indicates fluid velocity of the mitral regurgitation jet over time.

Spectral Doppler ultrasound acquisition may generally be performed using a continuous wave (CW) Doppler technique or a pulsed wave (PW) Doppler technique. For CW Doppler ultrasound acquisition, an ultrasound system may display a two-dimensional (2D) ultrasound image including a CW line. The user may manually adjust the location of the CW line to set the measurement location for the CW Doppler ultrasound data acquisition. Generally, the CW line corresponds to a longitudinal axis of the mitral regurgitation jet. The ultrasound system may acquire CW Doppler ultrasound data along the CW line, and display CW Doppler ultrasound information that identifies fluid velocity along the CW line over time. For PW Doppler ultrasound acquisition, the ultrasound system may display a 2D ultrasound image including a PW line and a PW gate that delineates a segment of the PW line. The user may manually adjust the location of the PW line and the location of the PW gate to set the measurement location for PW Doppler ultrasound data acquisition. Generally, the PW line corresponds to the longitudinal axis of the mitral regurgitation jet and the PW gate corresponds to the *vena contracta*. The ultrasound system may acquire PW Doppler ultrasound data along the PW line and within the PW gate, and display PW Doppler ultrasound information that identifies fluid velocity along the PW line and within the PW gate over time.

The foregoing techniques may generally require the user to manually select a particular 2D ultrasound image corresponding to a particular plane of the ROI of the subject, and manually set the CW line or the PW line and the PW gate in the particular 2D ultrasound image. This process may be time-consuming, inconvenient, cumbersome, and/or error prone because of, among other things, the three-dimensional (3D) nature of the relevant anatomy of the ROI. For example, in the case of measuring regurgitant volume, it might be difficult for the user to select a particular 2D ultrasound image that depicts a mitral regurgitant jet, and optimally set the CW line or the PW line and the PW gate in the particular 2D ultrasound image to correspond to the *vena contracta* of the mitral regurgitation jet.

Accordingly, the manual selection of a particular 2D ultrasound image and the manual selection of the CW line or the PW line and the PW gate might result in the consumption of processor and/or memory resources of the ultrasound system due to the extensive amount of manual user interactions with the ultrasound system. Additionally, the manual selection may result in inaccurate or erroneous *vena contracta* and/or regurgitant volume measurements due to sub-optimal placement of the CW line or the PW line and the PW gate. As such, a need exists for a technical improvement to user interfaces associated with ultrasound systems for setting the measurement location for CW Doppler ultrasound data acquisition and PW Doppler ultrasound data acquisition, and for a technical improvement to ultrasound systems for performing CW Doppler ultrasound data acquisition and PW Doppler ultrasound data acquisition.

SUMMARY

This summary introduces concepts that are described in more detail in the detailed description. It should not be used to identify essential features of the claimed subject matter, nor to limit the scope of the claimed subject matter.

In an aspect, an ultrasound system may comprise an ultrasound probe comprising a lens, an acoustic matching layer, an acoustic dematching layer, and a plurality of transducer elements; a memory configured to store instructions; and one or more processors configured to execute the instructions to: acquire four-dimensional (4D) color flow ultrasound data of a region of interest (ROI) of a subject; display a 4D color flow ultrasound image of the ROI of the subject based on the 4D color flow ultrasound data; receive a user input selecting a measurement location in the 4D color flow ultrasound image of the ROI of the subject; automatically acquire spectral Doppler ultrasound data corresponding to the measurement location based on the user input; and display spectral Doppler information corresponding to the spectral Doppler ultrasound data.

In another aspect, a method may include acquiring four-dimensional (4D) color flow ultrasound data of a region of interest (ROI) of a subject; displaying a 4D color flow ultrasound image of the ROI of the subject based on the 4D color flow ultrasound data; receiving a user input selecting a measurement location in the 4D color flow ultrasound image of the ROI of the subject; automatically acquiring spectral Doppler ultrasound data corresponding to the measurement location based on the user input; and displaying spectral Doppler information corresponding to the spectral Doppler ultrasound data.

In yet another aspect, a non-transitory computer-readable medium may store instructions that, when executed by one or more processors, cause the one or more processors to: acquire four-dimensional (4D) color flow ultrasound data of a region of interest (ROI) of a subject; display a 4D color flow ultrasound image of the ROI of the subject based on the 4D color flow ultrasound data; receive a user input selecting a measurement location in the 4D color flow ultrasound image of the ROI of the subject; automatically acquire spectral Doppler ultrasound data corresponding to the measurement location based on the user input; and display spectral Doppler information corresponding to the spectral Doppler ultrasound data.

DETAILED DESCRIPTION

As addressed above, the manual selection of a particular 2D ultrasound image and the manual selection of the CW line or the PW line and the PW gate might result in the consumption of processor and/or memory resources of the ultrasound system due to the extensive amount of user interactions with the ultrasound system. Additionally, the manual selection may result in inaccurate or erroneous measurements due to sub-optimal placement of the CW line or the PW line and the PW gate.

Some embodiments herein provide an ultrasound system that acquires 4D color flow ultrasound data of an ROI of a subject, displays a 4D color flow ultrasound image of the ROI of the subject based on the 4D color flow ultrasound data, receives a user input selecting a measurement location in the 4D color flow ultrasound image of the ROI of the subject, automatically acquires spectral Doppler ultrasound data corresponding to the measurement location based on the user input, and displays spectral Doppler information corresponding to the spectral Doppler ultrasound data.

The ultrasound system automatically acquires spectral Doppler ultrasound data corresponding to a measurement location that is selected by the user based on a single user input. For instance, the user inputs the user input by selecting the measurement location in the 4D color flow ultrasound image of the ROI of the subject. Accordingly, in this way, the ultrasound system reduces, or eliminates, the need of the user to manually select a particular 2D ultrasound image of the ROI and manually select a CW line or a PW line and a PW gate.

In this way, some embodiments herein provide an improvement in the technical field of ultrasound imaging by providing an improved mechanism for automatic spectral Doppler ultrasound data acquisition. Further, some embodiments provide an improvement to an ultrasound system by permitting the ultrasound system to automatically acquire spectral Doppler ultrasound data corresponding to a measurement location that is selected by the user based on a single user input. Further still, some embodiments herein provide an improved user interface for ultrasound systems by permitting the user to input a single user input that causes the ultrasound system to automatically acquires spectral Doppler ultrasound data corresponding to a measurement location that is selected by the user based on the single user input. The embodiments herein may conserve processor and/or memory resources of ultrasound systems by reducing, or eliminating, the extensive amount of user interactions associated with setting the measurement location for spectral Doppler data acquisition. Further, the embodiments herein may improve the accuracy of spectral Doppler information by reducing the amount of inaccurate or erroneous measurements due to sub-optimal placement of the CW line or the PW line and the PW gate.

Figure 1:
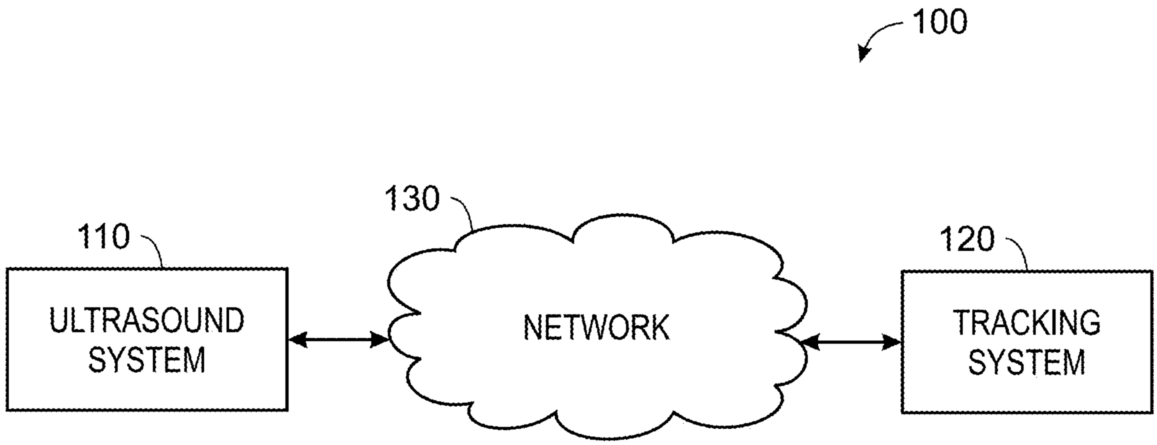
FIG. 1 is a diagram of an example system for automatic spectral Doppler ultrasound data acquisition.

FIG. 1 is a diagram of an example system 100 for automatic spectral Doppler ultrasound data acquisition. As shown in FIG. 1, the system 100 may include an ultrasound system 110, a tracking system 120, and a network 130.

The ultrasound system 110 may be configured to acquire ultrasound data of a region of interest of a subject. For example, the ultrasound system 110 may be a two-dimensional (2D) ultrasound system, a three-dimensional (3D) ultrasound system, a four-dimensional (4D) ultrasound system, a Doppler ultrasound system, or the like. The subject may be a person, an animal, a phantom, or the like. The region of interest may be any anatomical region of the subject. For example, the region of interest may be a heart, a brain, an organ, a blood vessel, or the like.

The tracking system 120 may be configured to acquire tracking data of an ultrasound probe of the ultrasound system 100. For example, the tracking system 120 may be an electromagnetic tracking system, an optical tracking system, an acoustic tracking system, an inertial tracking system, an ultrasound tracking system, or the like.

The network 130 may permit communication between the ultrasound system 110 and the tracking system 120. For example, the network 130 may be a local area network (LAN), a wide area network (WAN), a metropolitan area network (MAN), a cellular network, a private network, an ad hoc network, an intranet, the Internet, a fiber optic-based network, a wired network, a wireless network, or the like, and/or a combination of these or other types of networks.

The number and arrangement of the system 100 are provided as an example. In practice, the system 100 may include additional systems, fewer systems, different systems, or differently arranged systems than those shown in FIG. 1. Additionally, or alternatively, a set of systems (e.g., one or more systems) of the system 100 may be integrated into a single system, and/or perform one or more functions described as being performed by another system, or set of systems, of the system 100.

Figure 2:
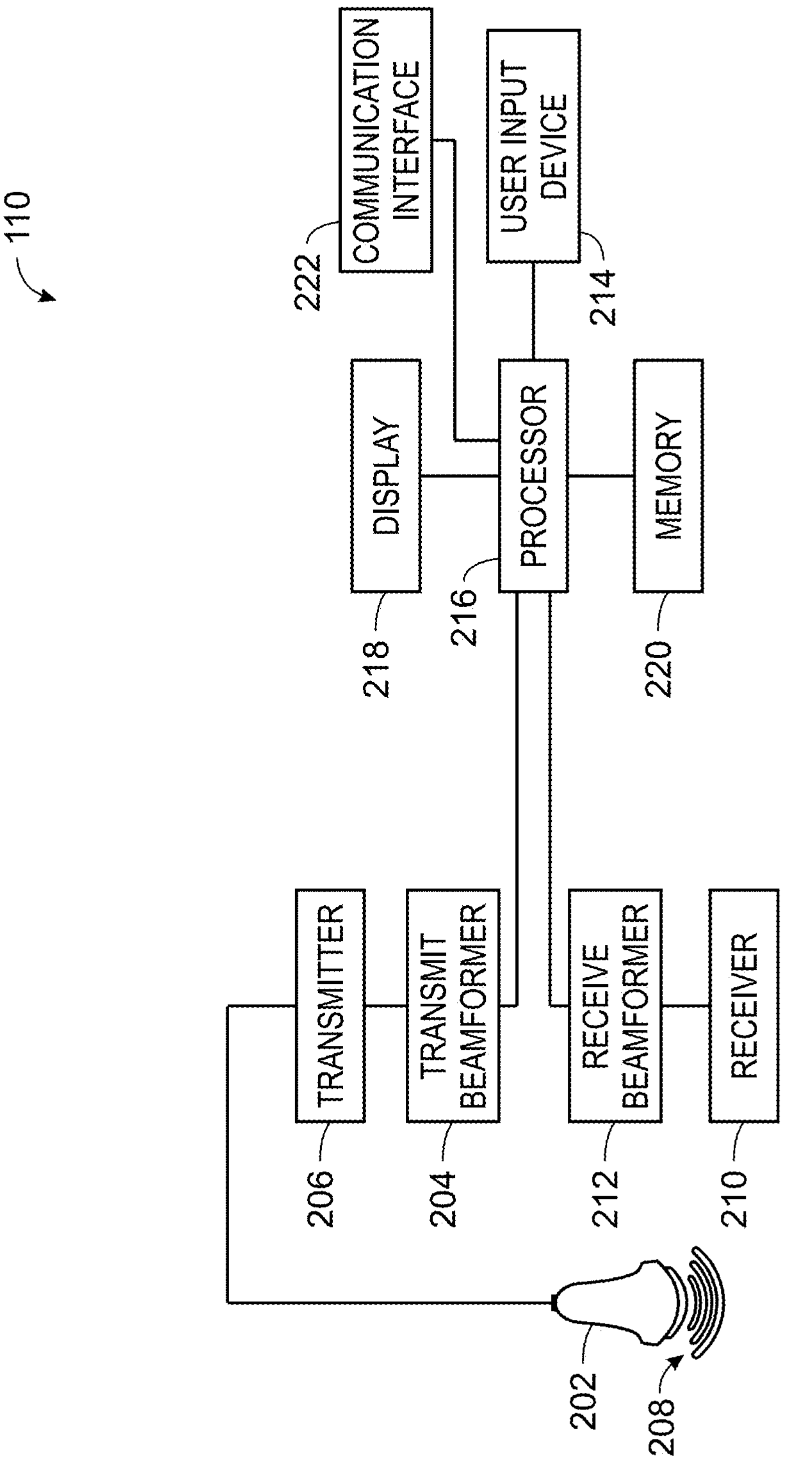
FIG. 2 is a diagram of example components of the ultrasound system for automatic spectral Doppler ultrasound data acquisition.

FIG. 2 is a diagram of example components of the ultrasound system 110 for automatic spectral Doppler ultrasound data acquisition. As shown in FIG. 2, the ultrasound system 110 may include an ultrasound probe 202, a transmit beamformer 204, a transmitter 206, elements 208, a receiver 210, a receive beamformer 212, a user input device 214, a processor 216, a display 218, a memory 220, and a communication interface 222. The foregoing components may be connected via wired or wireless connections.

The ultrasound probe 202 may be configured to acquire ultrasound data. For example, the ultrasound probe 202 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 202 may be a transthoracic echocardiogram (TTE) probe, a transesophageal echocardiography (TEE) probe, a 4D intracardiac echocardiography (ICE) probe, or the like. According to an embodiment, the ultrasound probe 202 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data.

The transmit beamformer 204 may be configured to apply delay times to electrical signals provided to the elements 208 to focus corresponding ultrasound signals at the region of interest. The transmitter 206 may be configured to transmit electrical signals to the elements 208 to drive the elements 208 to emit ultrasound signals towards the region of interest. The elements 208 may be configured to receive the electrical signals from the transmitter 206, convert the electrical signals into ultrasound signals, and emit the ultrasound signals towards the region of interest. The elements 208 may be configured to receive echo ultrasound signals that are back-scattered by the region of interest, convert the echo ultrasound signals into electrical signals, and provide the electrical signals to the receiver 210. The receiver 210 may be configured to receive electrical signals from the elements 208, and provide the electrical signals to the receive beamformer 212. The receive beamformer 212 may apply delay times to the electrical signals received from the elements 208.

The user input device 214 may be configured to receive a user input, and provide the user input to the processor 216. For example, the user input device 214 may be a touch screen display, a user interface, a keyboard, a keypad, a mouse, a button, a switch, a microphone, or the like. Additionally, or alternatively, the user input device 214 may be configured to sense information. For example, the user input device 214 may sense information from an electromagnetic positioning system, an inertial measurement system, an accelerometer, a gyroscope, an actuator, or the like.

The processor 216 may be configured to perform the operations as described herein. For example, the processor 216 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 216 may be implemented in hardware, firmware, or a combination of hardware and software. The processor 216 may include one or more processors 216 configured to perform the operations described herein. For example, a single processor 216 may be configured to perform all of the operations described herein. Alternatively, multiple processors 216, collectively, may be configured to perform all of the operations described herein, and each of the multiple processors 216 may be configured to perform a subset of the operations descried herein. For example, a first processor 216 may perform a first subset of the operations described herein, a second processor 216 may be configured to perform a second subset of the operations described herein, etc.

The processor 216 may be configured to control the ultrasound probe 202 to acquire ultrasound data. The processor 216 may be configured to control which of the elements 208 are active, and control the shape of a beam emitted from the ultrasound probe 202. The processor 216 may generate ultrasound images for display. For example, the processor 216 may generate B-mode images, color Doppler images, M-mode images, color M-mode images, or the like. The ultrasound images may be 4D images, 3D images, 2D images, single plane images, bi-plane images, three-plane images, multi-plane images, or the like. The ultrasound images may correspond to various anatomical planes (e.g., sagittal, coronal, and transverse) of the region of interest.

The display 218 may be configured to display information. For example, the display 218 may be a user interface, a monitor, an LED display, a cathode ray tube, a projector display, a touchscreen, tablet computer, mobile phone, or the like. The display 218 may display ultrasound images based on the ultrasound data in real-time. For example, the display 218 may display the ultrasound images within one second, two seconds, five seconds, etc., of the ultrasound data being acquired by the ultrasound probe 202.

The memory 220 may be configured to store information and/or instructions for use by the processor 216. The memory 220 may be a non-transitory computer-readable medium. For example, the memory 220 may be a random access memory (RAM), a read only memory (ROM), and/or another type of dynamic or static storage device (e.g., a flash memory, a magnetic memory, and/or an optical memory) that stores information and/or instructions for use by the processor 216. The memory 220 may be configured to store instructions that, when executed by the processor 216, cause the processor 216 to perform the operations described herein.

The communication interface 222 may be configured to enable the processor 216 to communicate with other systems, such as via a wired connection, a wireless connection, or a combination of wired and wireless connections. For example, the communication interface 222 may include an Ethernet interface, an optical interface, a coaxial interface, an infrared interface, a radio frequency (RF) interface, a universal serial bus (USB) interface, a Wi-Fi interface, a cellular network interface, or the like.

The number and arrangement of the components of the ultrasound system 110 shown in FIG. 2 are provided as an example. In practice, the ultrasound system 110 may include additional components, fewer components, different components, or differently arranged components than those shown in FIG. 2. Additionally, or alternatively, a set of components (e.g., one or more components) of the ultrasound system 110 may perform one or more functions described as being performed by another set of components of the ultrasound system 110.

Figure 3:
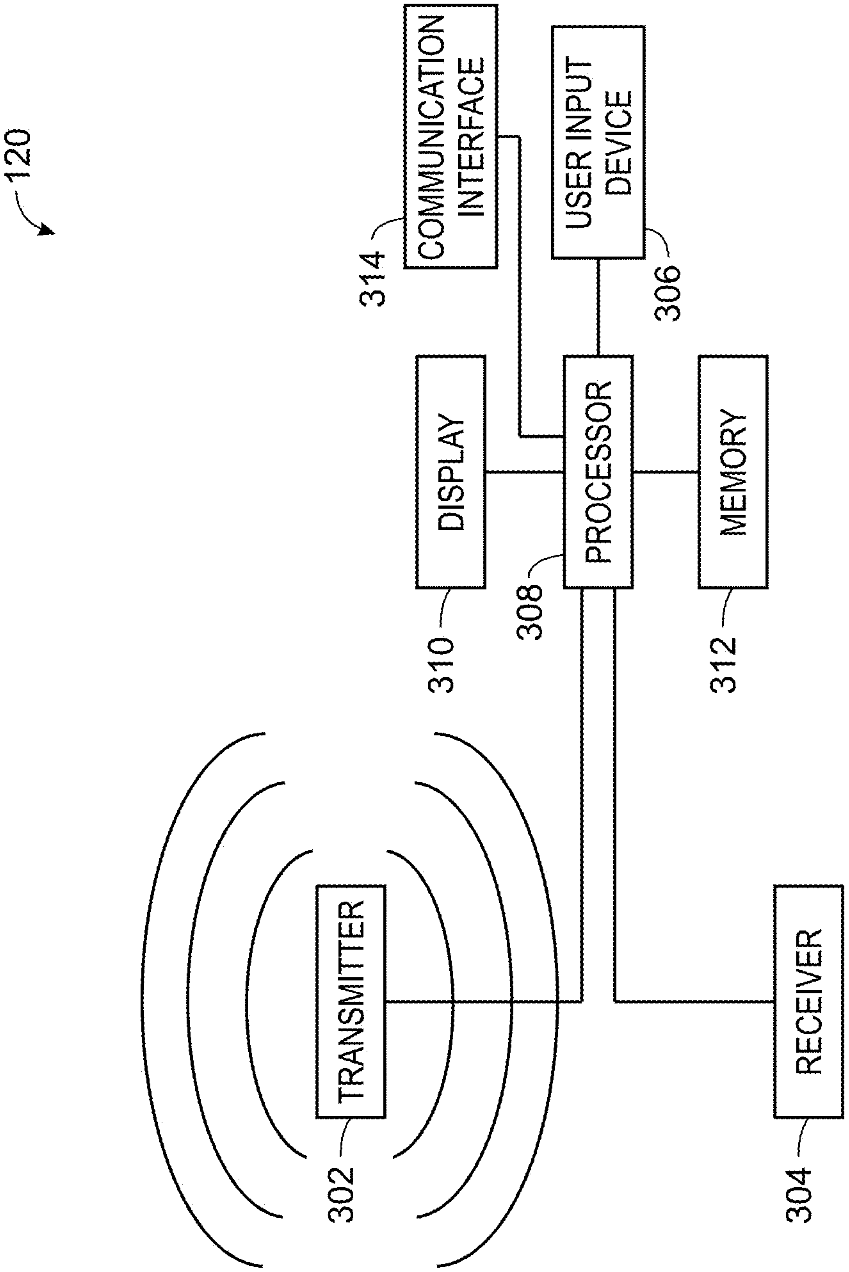
FIG. 3 is a diagram of example components of a tracking system.

FIG. 3 is a diagram of example components of a tracking system 120. As shown in FIG. 3, the tracking system 120 may include a transmitter 302, a receiver 304, a user input device 306, a processor 308, a display 310, a memory 312, and a communication interface 314.

The transmitter 302 may be configured to generate a magnetic field. The receiver 304 may be configured to output a signal in response to the magnetic field generated by the transmitter 302. The processor 308 may receive the output signal from the receiver 304, and acquire tracking data that identifies a position and/or an orientation of the receiver 304. According to an embodiment, the receiver 304 may be attached to the ultrasound probe 202 to track a position and/or an orientation of the ultrasound probe 202.

The user input device 306 may be configured to receive a user input, and provide the user input to the processor 308. For example, the user input device 306 may be a touch screen display, a keyboard, a keypad, a mouse, a button, a switch, a microphone, or the like. Additionally, or alternatively, the user input device 306 may be configured to sense information. For example, the user input device 306 may sense information from an electro-magnetic positioning system, an inertial measurement system, an accelerometer, a gyroscope, an actuator, or the like.

The processor 308 may be configured to perform the operations as described herein. For example, the processor 308 may be a CPU, a GPU, an APU, a microprocessor, a microcontroller, a DSP, an FPGA, an ASIC, or the like. The processor 308 may be implemented in hardware, firmware, or a combination of hardware and software. The processor 308 may include one or more processors 308 configured to perform the operations described herein. For example, a single processor 308 may be configured to perform all of the operations described herein. Alternatively, multiple processors 308, collectively, may be configured to perform all of the operations described herein, and each of the multiple processors 308 may be configured to perform a subset of the operations descried herein. For example, a first processor 308 may perform a first subset of the operations described herein, a second processor 308 may be configured to perform a second subset of the operations described herein, etc.

The processor 308 may be configured to control the transmitter 308 to acquire tracking data. The processor 308 may be configured to control excitations of the transmitter 302 to generate a magnetic field. The processor 308 may acquire tracking data based on controlling the transmitter 302.

The display 310 may be configured to display information. For example, the display 310 may be a monitor, an LED display, a cathode ray tube, a projector display, a touchscreen, tablet computer, mobile phone, or the like. The display 310 may display the tracking data in real-time. For example, the display 310 may display the tracking data within one second, two seconds, five seconds, etc., of the tracking data being acquired.

The memory 312 may be configured to store information and/or instructions for use by the processor 308. The memory 312 may be a non-transitory computer-readable medium. For example, the memory 312 may be a RAM, a ROM, a flash memory, a magnetic memory, an optical memory, or the like. The memory 312 may be configured to store instructions that, when executed by the processor 308, cause the processor 308 to perform the operations described herein.

The communication interface 314 may be configured to enable the processor 308 to communicate with other systems, such as via a wired connection, a wireless connection, or a combination of wired and wireless connections. For example, the communication interface 314 may include an Ethernet interface, an optical interface, a coaxial interface, an infrared interface, an RF interface, a USB interface, a Wi-Fi interface, a cellular network interface, or the like.

The number and arrangement of the components of the tracking system 120 shown in FIG. 3 are provided as an example. In practice, the tracking system 120 may include additional components, fewer components, different components, or differently arranged components than those shown in FIG. 3. Additionally, or alternatively, a set of components (e.g., one or more components) of the tracking system 120 may perform one or more functions described as being performed by another set of components of the tracking system 120.

Although FIG. 3 depicts the tracking system 120 as being an electromagnetic tracking system, it should be understood that the embodiments herein are applicable to other types of tracking systems, such as optical tracking systems, acoustic tracking systems, ultrasound tracking systems, or the like.

Figure 4:
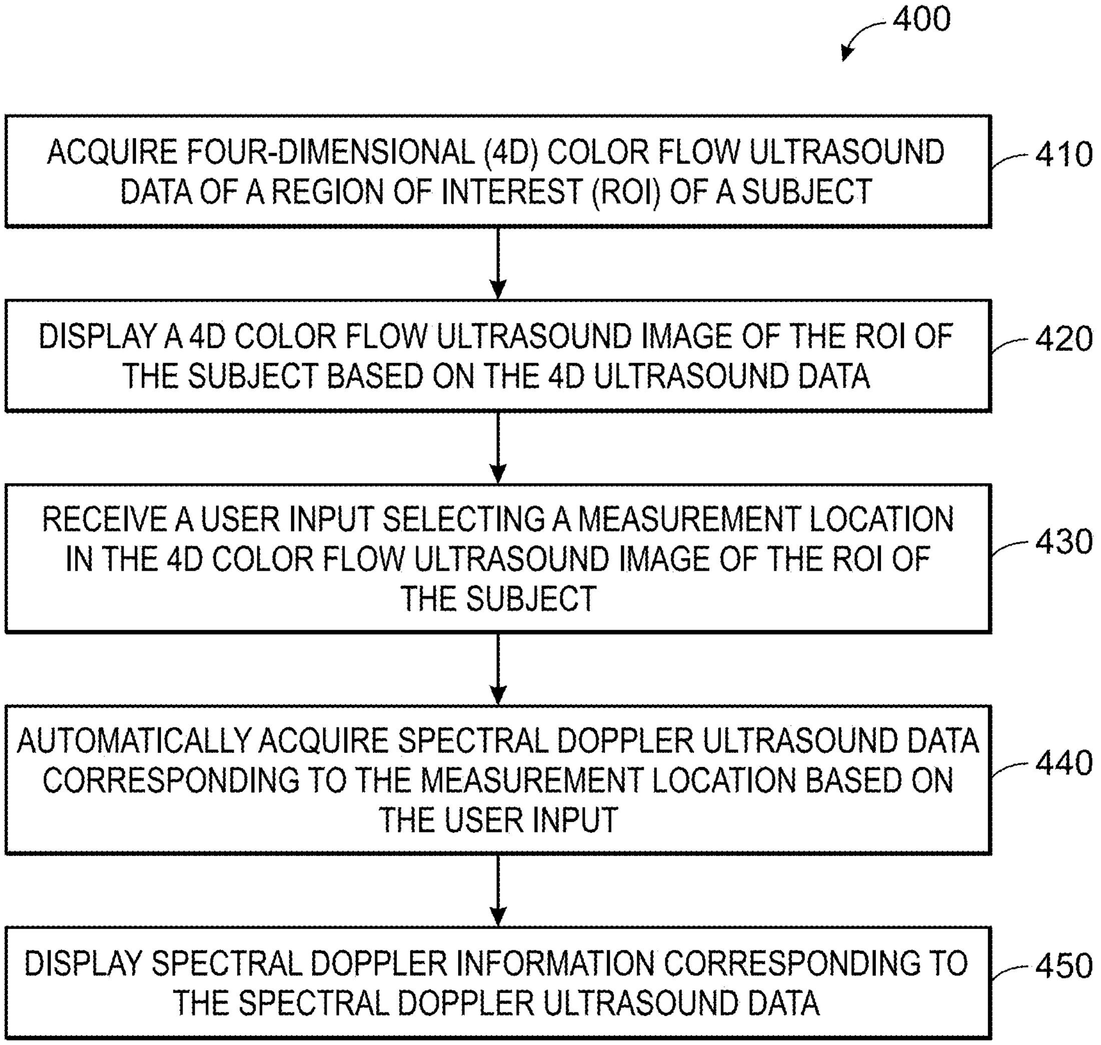
FIG. 4 is a flowchart of an example process for automatic spectral Doppler ultrasound data acquisition.

FIG. 4 is a flowchart of an example process 400 for automatic spectral Doppler ultrasound data acquisition. According to an embodiment, one or more operations of FIG. 4 may be performed by the processor 216. Additionally, or alternatively, one or more operations of FIG. 4 may be performed by another component, or set of components, of the ultrasound system 110, such as the ultrasound probe 202, the transmit beamformer 204, the transmitter 206, the elements 208, the receiver 210, the receive beamformer 212, the user input device 214, the display 218, the memory 220, and/or the communication interface 222.

As shown in FIG. 4, the process 400 may include acquiring four-dimensional (4D) color flow ultrasound data of a region of interest (ROI) of a subject (operation 410). For example, the ultrasound system may acquire 4D color flow ultrasound data of an ROI of a subject. The ultrasound system 110 may acquire the 4D color flow ultrasound data of the ROI of the subject based on the user manipulating the ultrasound probe 202 with respect to the subject. For example, the user may manipulate and position the ultrasound probe 202 with respect to the subject to acquire the 4D color flow ultrasound data of the ROI of the subject. The ROI of the subject may be any anatomical region of the subject. For example, the ROI may be the heart, the left ventricle, the left atrium, the right ventricle, the right atrium, the mitral valve, the aortic valve, the tricuspid valve, the pulmonary valve, or the like. Alternatively, the ROI may be a non-cardiac region, such as the liver, the pancreas, or the like. The 4D color flow ultrasound data may depict a regurgitant jet. The regurgitant jet may be a mitral regurgitant jet, an aortic regurgitant jet, a tricuspid regurgitant jet, a pulmonary regurgitant jet, or the like.

As further shown in FIG. 4, the process 400 may include displaying a 4D color flow ultrasound image of the ROI of the subject based on the 4D color flow ultrasound data (operation 420). For example, the ultrasound system 110 may display a 4D color flow ultrasound image of the ROI of the subject based on the 4D color flow ultrasound data. The 4D color flow ultrasound image may depict the ROI and fluid flow in the ROI over time. In this way, the user may manipulate and position the ultrasound probe 202 with respect to the subject, which causes the ultrasound system 110 to display the 4D color flow ultrasound image. Further, in this way, the user may view the 4D color flow ultrasound image, and adjust the positon of the ultrasound probe 202 with respect to the ROI of the subject to position the ultrasound probe 202 to image a particular structure of interest in the ROI. As an example, the structure of interest may be a regurgitant jet. The ultrasound system 110 may display the 4D color flow ultrasound image, and may display one or more other ultrasound images. For example, the ultrasound system 110 may display multiplanar reconstruction (MPR) slices associated with the 4D color flow ultrasound image.

As further shown in FIG. 4, the process 400 may include receiving a user input selecting a measurement location in the 4D color flow ultrasound image of the ROI of the subject (operation 430). For example, the ultrasound system may receive a user input selecting a measurement location in the 4D color flow ultrasound image of the ROI of the subject. The user may provide the user input by interacting with the user input device 214 of the ultrasound system 110. For example, the user may provide a user input on a volume rendering or on a two-dimensional (2D) slice of the 4D color flow ultrasound data. The user input may select a measurement location in the 4D color flow ultrasound image. In this way, the user may provide a single input that causes the ultrasound system 110 to acquire spectral Doppler ultrasound data corresponding to the measurement location, as described below.

As further shown in FIG. 4, the process 400 may include automatically acquiring spectral Doppler ultrasound data corresponding to the measurement location based on the user input (operation 440). For example, the ultrasound system may automatically acquire spectral Doppler ultrasound data corresponding to the measurement location based on the user input. The spectral Doppler ultrasound data may be CW Doppler ultrasound data, PW Doppler ultrasound data, or the like.

According to an embodiment, the ultrasound system 110 may determine a CW line for CW Doppler ultrasound data acquisition based on the measurement location. The ultrasound system 110 may determine measurement location position information of the measurement location. The measurement location position information may identify a position of a measurement location in a coordinate space of the ultrasound system 110. For example, the ultrasound system 110 may determine a 3D coordinate of the measurement location based on tracking data of the ultrasound probe 202 acquired by the tracking system 120. The ultrasound system 110 may determine ultrasound probe position information of the ultrasound probe 202. The ultrasound probe position information may identify a position of the ultrasound probe 202 in the coordinate space of the ultrasound system 110. For example, the ultrasound system 110 may determine a 3D coordinate of the ultrasound probe 202 based on tracking data of the ultrasound probe 202 acquired by the tracking system 120. The ultrasound system 110 may determine a CW line based on the measurement location position information of the measurement location and the ultrasound probe position information of the ultrasound probe 202. For example, the ultrasound system 110 may determine a CW line that coincides with the 3D coordinate of the measurement point and the 3D coordinate of the ultrasound probe 202. The ultrasound system 110 may determine an azimuth, a tilt, and an elevation of the CW line.

According to an embodiment, the ultrasound system 110 may determine a PW line for PW Doppler ultrasound data acquisition based on the measurement location. The ultrasound system 110 may determine measurement location position information of the measurement location. The measurement location position information may identify a position of the measurement location in a coordinate space of the ultrasound system 110. For example, the ultrasound system 110 may determine a 3D coordinate of the measurement location based on tracking data of the ultrasound probe 202 acquired by the tracking system 120. The ultrasound system 110 may determine ultrasound probe position information of the ultrasound probe 202. The ultrasound probe position information may identify a position of the ultrasound probe 202 in the coordinate space of the ultrasound system 110. For example, the ultrasound system 110 may determine a 3D coordinate of the ultrasound probe 202 based on tracking data of the ultrasound probe 202 acquired by the tracking system 120. The ultrasound system 110 may determine a PW line based on the measurement location position information of the measurement location and the ultrasound probe position information of the ultrasound probe 202. For example, the ultrasound system 110 may determine a PW line that coincides with the 3D coordinate of the measurement point and the 3D coordinate of the ultrasound probe 202. The ultrasound system 110 may determine an azimuth, a tilt, and an elevation of the PW line.

According to an embodiment, the ultrasound system 110 may determine a PW gate for PW Doppler ultrasound data acquisition. The PW gate may be a segment along the PW line. The PW gate may also be referred to as a "PW sample." The ultrasound system 110 may determine the PW gate using a predetermined configuration for the PW gate. For example, the predetermined configuration may define a length of the PW gate, may define a length proximal to the measurement position, may define a length distal to the measurement location, or the like. Alternatively, the ultrasound system 110 may determine the PW gate based on a characteristic of the structure of interest in the ROI. For example, the ultrasound system 110 may determine the PW gate based on size of the structure of interest, based on a location of the structure of interest, or the like.

According to an embodiment, the ultrasound system 110 may acquire the spectral Doppler data based on determining the CW line. For example, the ultrasound system 110 may control the ultrasound probe 202 to acquire CW Doppler ultrasound data along the CW line. According to another embodiment, the ultrasound system 110 may acquire the spectral Doppler data based on determining the PW line and the PW gate. For example, the ultrasound system 110 may control the ultrasound probe 202 to acquire PW Doppler ultrasound data along the PW line and within the PW gate.

According to an embodiment, the ultrasound system 110 may automatically acquire the spectral Doppler ultrasound data corresponding to the measurement location based on the user input. As used herein, "automatically acquire" may refer to the automatic acquisition of the spectral Doppler ultrasound data based on the single user input that selects the measurement location in the 4D color flow ultrasound image of the ROI of the subject. Restated, the ultrasound system 110 may automatically determine the CW line or the PW line and the PW gate based on the single user input that selects the measurement location in the 4D color flow ultrasound image of the ROI of the subject, and acquire the CW Doppler ultrasound data or the PW Doppler ultrasound data using the CW line or the PW line and the PW gate. Put yet another way, the ultrasound system 110 may acquire the spectral Doppler data without requiring the user to manually set the CW line or the PW line and the PW gate.

As further shown in FIG. 4, the process 400 may include displaying spectral Doppler information corresponding to the spectral Doppler ultrasound data (operation 450). For example, the ultrasound system may display spectral Doppler information corresponding to the spectral Doppler ultrasound data. According to an embodiment, the spectral Doppler information may be CW Doppler information. The CW Doppler information may identify a velocity of fluid along the CW line. According to another embodiment, the spectral Doppler information may be PW Doppler information. The PW Doppler information may identify fluid velocity along the PW line and within the PW gate over time.

Although FIG. 4 depicts a particular set of operations, it should be understood that other embodiments may include different operations, such as more operations, less operations, or the like. Further, although FIG. 4 depicts a particular sequence of operations, it should be understood that other embodiments may include a different sequence of operations. Further still, one or more operations may be performed simultaneously, concurrently, etc.

FIGS. 5A-5D are diagrams of an example process 500 for automatic spectral Doppler ultrasound data acquisition.

Figure 5A:
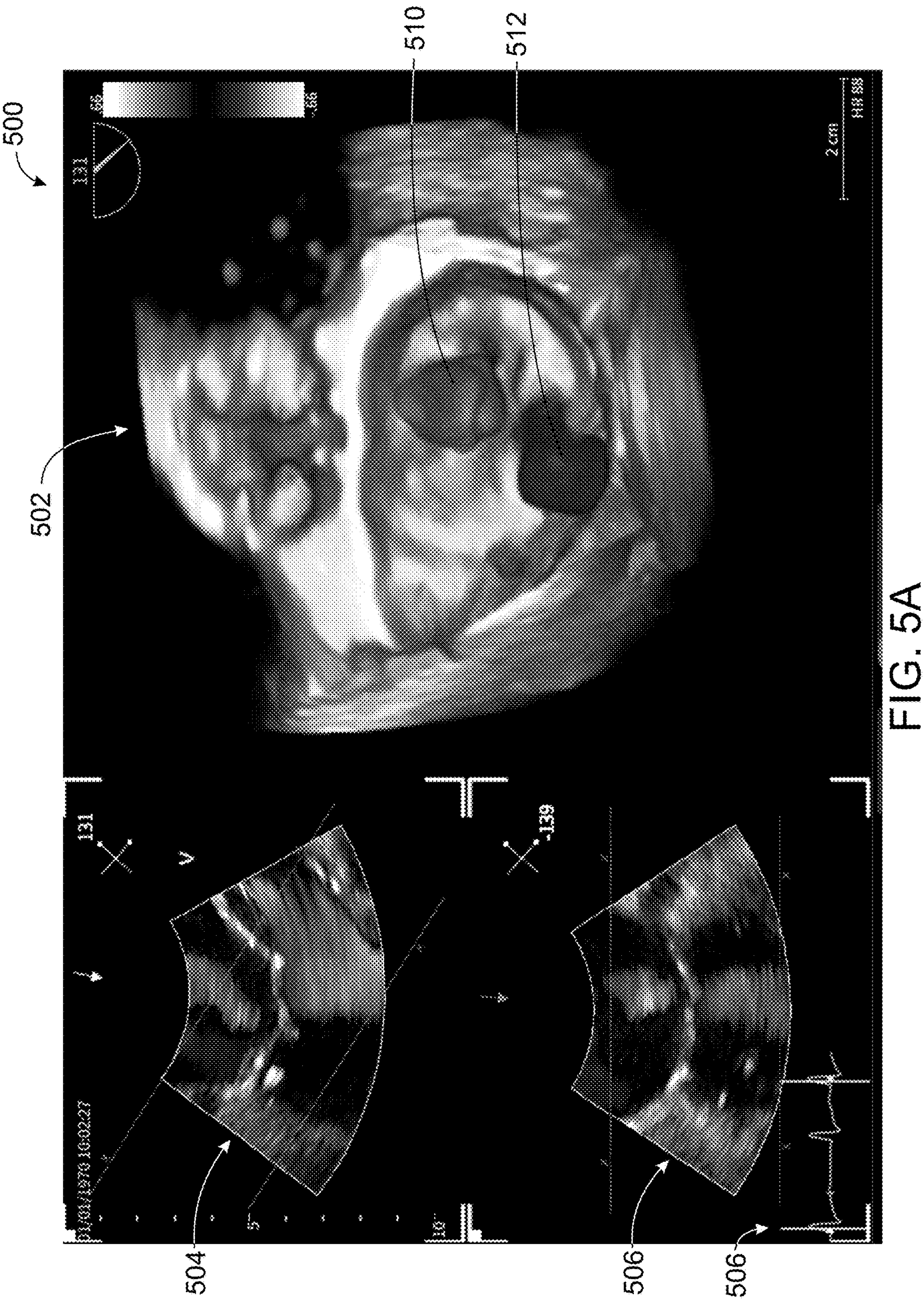
FIGS. 5A-5D are diagrams of an example process for automatic spectral Doppler ultrasound data acquisition.

As shown in FIG. 5A, the ultrasound system 110 may display a 4D color flow ultrasound image 502 of an ROI of a subject based on 4D color flow ultrasound data. Further, as shown, the ultrasound system 110 may display a first 2D color flow ultrasound image 504 corresponding to a first slice of the 4D color flow ultrasound image 502, and a second 2D color flow ultrasound image 506 corresponding to a second slide of the 4D color flow ultrasound image 502. Further, as shown, the ultrasound system 110 may display an ECG 508 that delineates a portion of the cardiac cycle to which the 4D color flow ultrasound image 502 corresponds. As further shown in the 4D color flow ultrasound image 502 of FIG. 5A, the ultrasound system 110 may display a first jet 510 having flow in a first direction, and a second jet 512 having flow in a second direction.

Figure 5B:
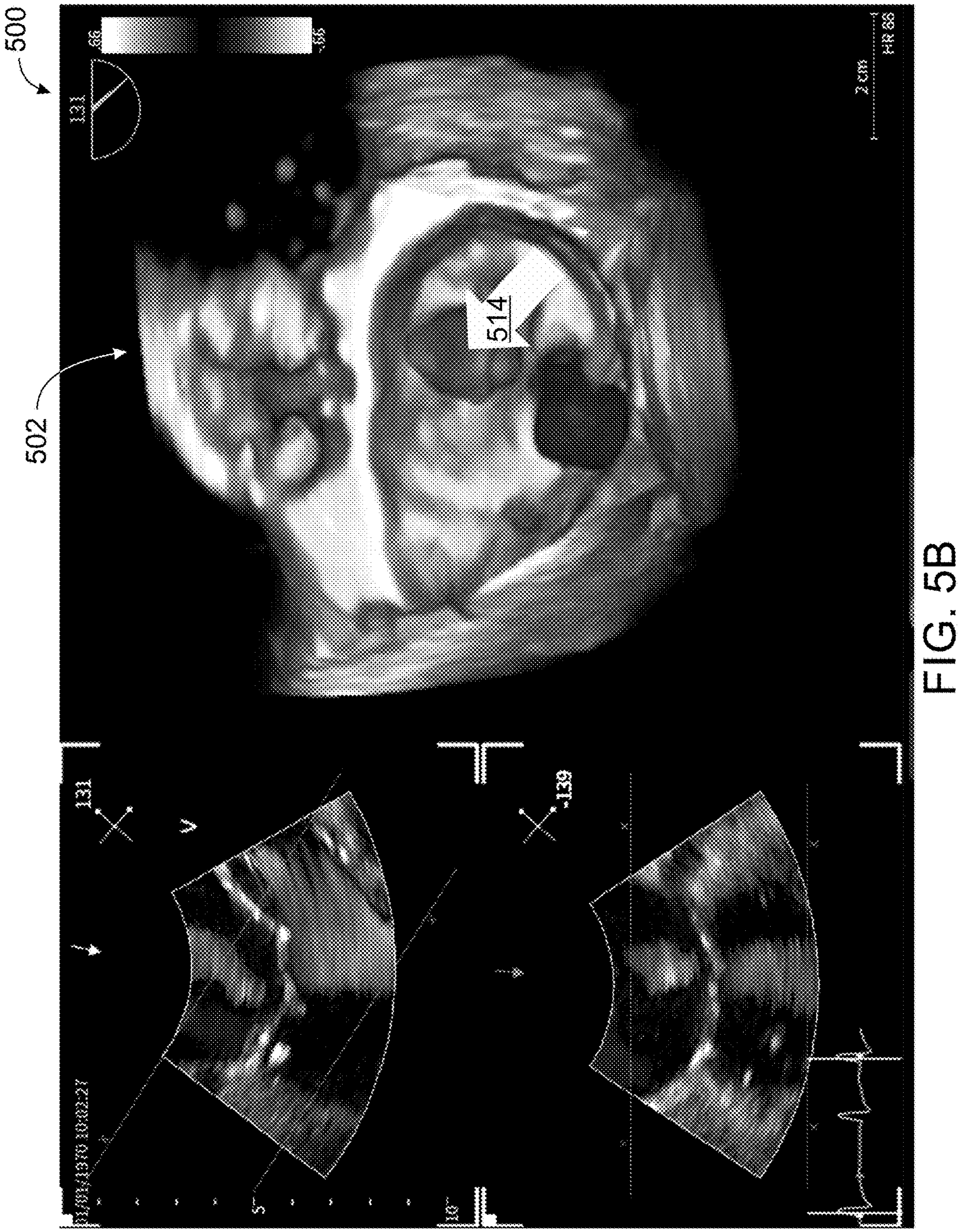

As shown in FIG. 5B, the ultrasound system 110 may receive a user input selecting a measurement location 514 in the 4D color flow ultrasound image 502 of the ROI of the subject. For example, as shown, the user may interact with a user interface of the ultrasound system 110 to move a user interface element in the form of an arrow to a measurement location 514 in the 4D color flow ultrasound image 502 of the ROI of the subject. The measurement location 514 may coincide with the first jet 510.

Figure 5C:
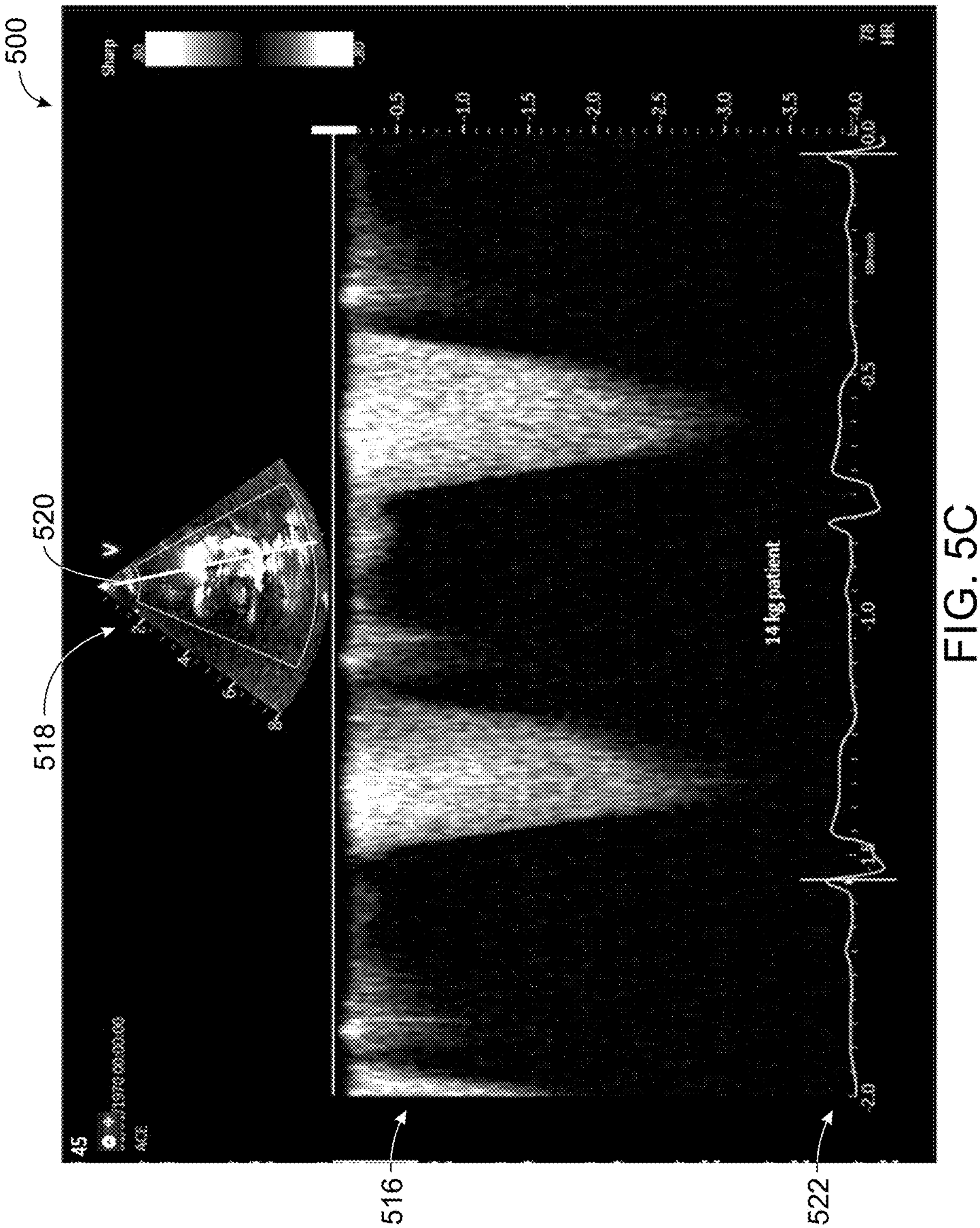

As shown in FIG. 5C, the ultrasound system 110 may automatically acquire CW Doppler ultrasound data corresponding to the measurement location based on the user input, and display CW Doppler information 516 corresponding to the CW Doppler ultrasound data. For example, as shown in reference to the 2D ultrasound image 518, the ultrasound system 110 may determine a CW line 520 based on the measurement location 514, and acquire CW Doppler ultrasound data along the CW line 520. Further, the ultrasound system 110 may display the CW Doppler information 516 that depicts fluid velocity over time. Further still, the ultrasound system 110 may display an ECG 522 that depicts the portion of the cardiac cycle to which the CW Doppler information 516 corresponds.

Figure 5D:
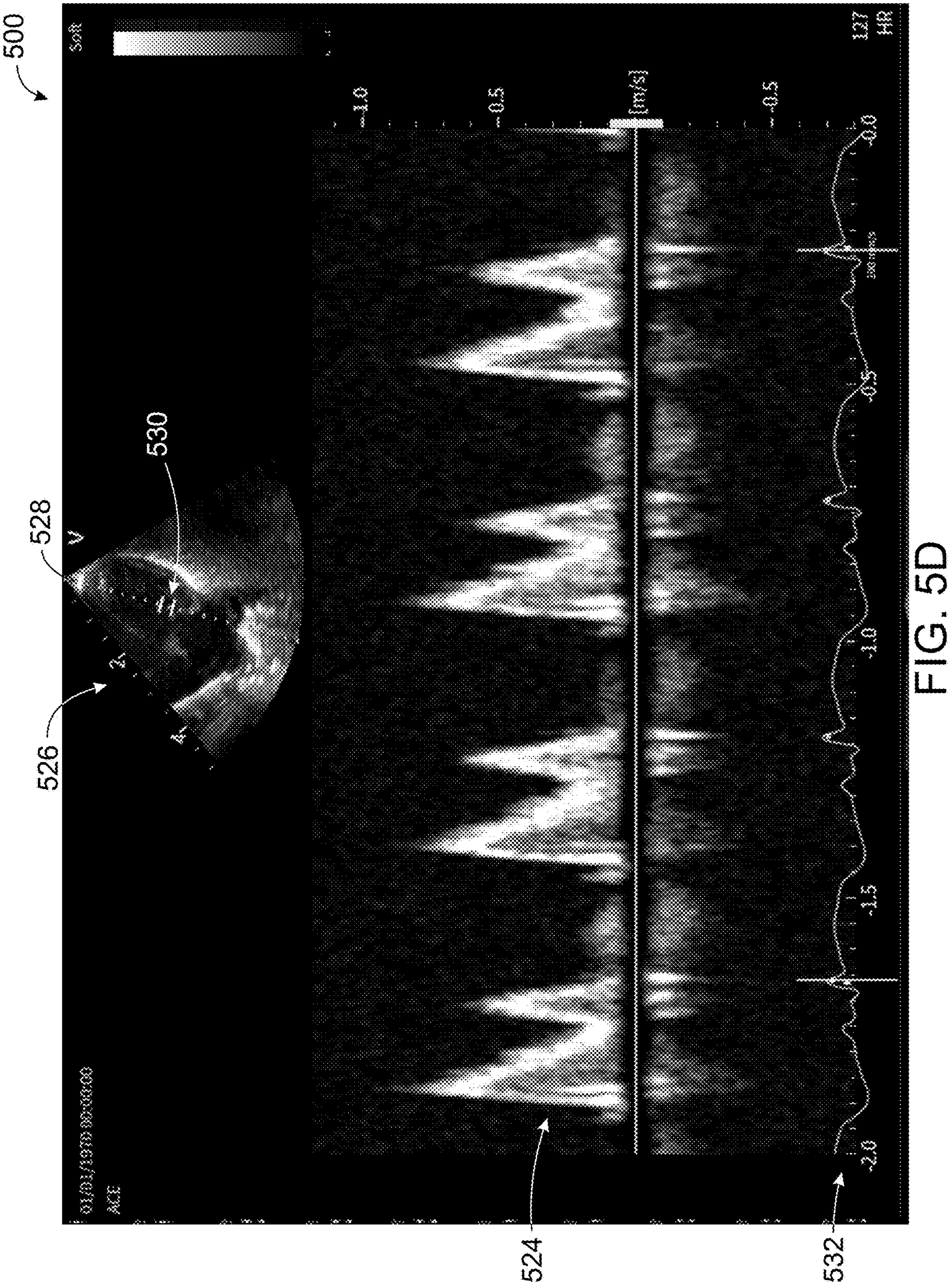

As shown in FIG. 5D, the ultrasound system 110 may automatically acquire PW Doppler ultrasound data corresponding to the measurement location based on the user input, and display PW Doppler information 524 corresponding to the PW Doppler ultrasound data. For example, as shown in reference to the 2D ultrasound image 526, the ultrasound system 110 may determine a PW line 528 and a PW gate 530 based on the measurement location 514, and acquire PW Doppler ultrasound data along the PW line 528 and within the PW gate 530. Further, the ultrasound system 110 may display the PW Doppler information 524 that depicts fluid velocity over time. Further still, the ultrasound system 110 may display an ECG 532 that depicts the portion of the cardiac cycle to which the PW Doppler information 524 corresponds.

Figure 6:
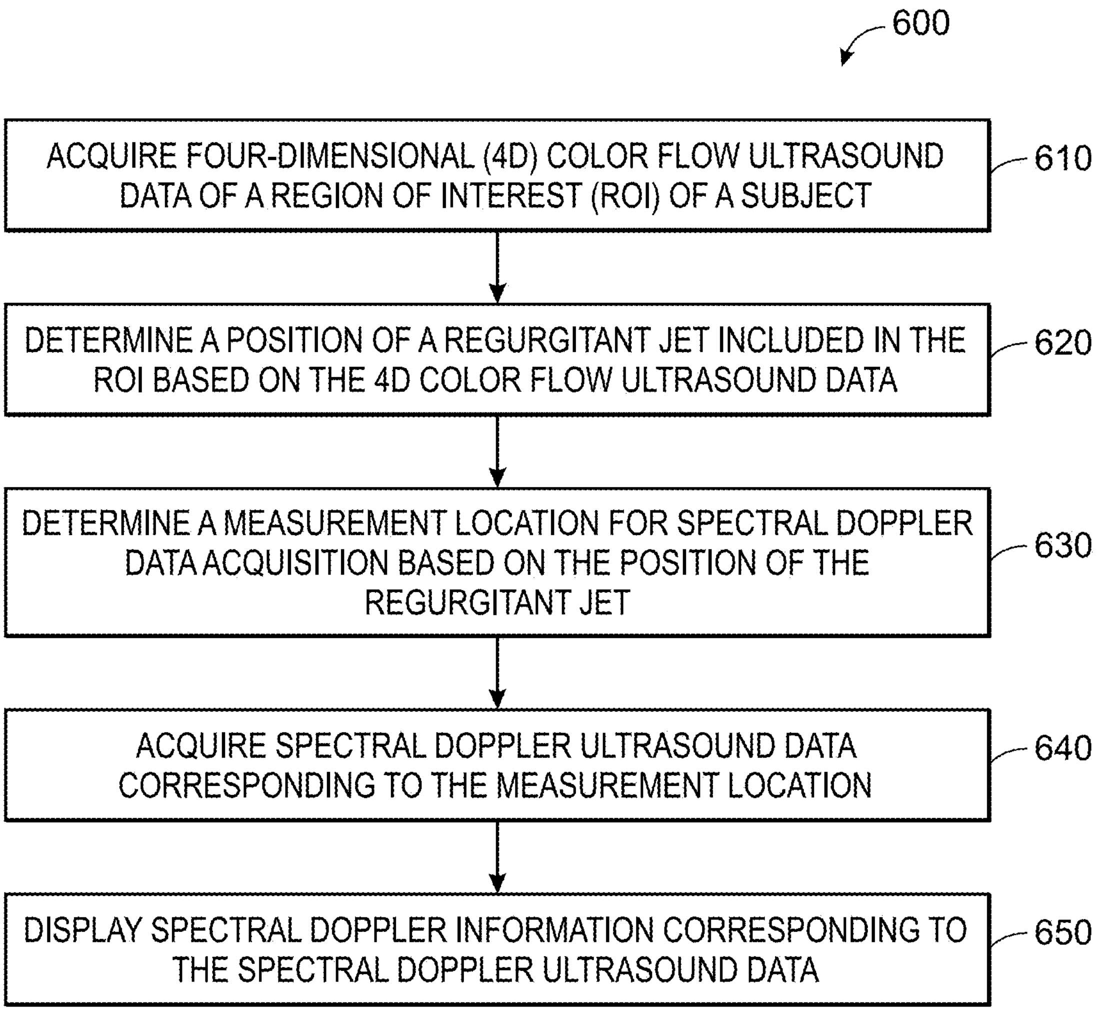
FIG. 6 is a flowchart of an example process for automatic spectral Doppler ultrasound data acquisition based on a determined position of a regurgitant jet.

FIG. 6 is a flowchart of an example process 600 for automatic spectral Doppler ultrasound data acquisition based on a determined position of a regurgitant jet. According to an embodiment, one or more operations of FIG. 6 may be performed by the processor 216. Additionally, or alternatively, one or more operations of FIG. 4 may be performed by another component, or set of components, of the ultrasound system 110, such as the ultrasound probe 202, the transmit beamformer 204, the transmitter 206, the elements 208, the receiver 210, the receive beamformer 212, the user input device 214, the display 218, the memory 220, and/or the communication interface 222.

As shown in FIG. 6, the process 600 may include acquiring four-dimensional (4D) color flow ultrasound data of a region of interest (ROI) of a subject (operation 610). For example, the ultrasound system 110 may acquire 4D color flow ultrasound data of an ROI of a subject in a similar manner as described above in connection with operation 410 of FIG. 4.

As further shown in FIG. 6, the process 600 may include determining a position of a regurgitant jet included in the ROI based on the 4D color flow ultrasound data (operation 620). For example, the ultrasound system 110 may determine a position of a regurgitant jet in the ROI based on the 4D color flow ultrasound data. The position of the regurgitant jet may be a position of an origin of the regurgitant jet, a position of a *vena contracta* of the regurgitant jet, or the like.

According to an embodiment, the ultrasound system 110 may determine the position of the regurgitant jet based on an image processing technique. For example, the image processing technique may be a segmentation technique, a pattern matching technique, a feature extraction technique, an image analysis technique, an edge detection technique, an image registration technique, or the like.

According to an embodiment, the ultrasound system 110 may determine the position of the regurgitant jet based on an output of an artificial intelligence (AI) model. The AI model may be a convolutional neural network (CNN) model, a residual neural network, a random forest model, a decision tree model, an artificial neural network (ANN), a Naïve Bayes model, a decision tree, a recurrent neural network (RNN), a logistic regression model, a support vector machine, or the like. According to an embodiment, the ultrasound system 110 may use one or more AI models. The one or more AI models may be associated with a training phase, a deployment phase, and a monitoring phase. In the training phase, the ultrasound system 110 may receive and process training data to generate a trained model. The training data may be generated, received, or otherwise obtained from internal and/or external resources.

Generally, the trained model may include a set of variables (e.g., nodes, neurons, filters, or the like) that are tuned (e.g., weighted, biased, or the like) to different values via the application of the training data. According to an embodiment, the training process may employ supervised, unsupervised, semi-supervised, and/or reinforcement learning processes to train the model. According to an embodiment, a portion of the training data may be withheld during training and/or used to validate the trained model.

For supervised learning processes, the training data may include labels or scores that may facilitate the training process by providing a ground truth. For example, the labels or scores may indicate an output of the model. Training may proceed by feeding a training dataset including the training data into the model. The model may have variables set at initialized values (e.g., at random, based on Gaussian noise, based on pre-trained values, or the like). The model may generate an output based on the training dataset being input to the model. The output may be compared with the corresponding label or score (e.g., the ground truth) indicating the known output, which may then be back-propagated through the model to adjust the values of the variables. This process may be repeated for a plurality of samples at least until a determined loss or error is below a predefined threshold. According to an embodiment, some of the training data may be withheld and used to further validate or test the trained model.

For unsupervised learning processes, the training data may not include pre-assigned labels or scores to aid the learning process. Instead, unsupervised learning processes may include clustering, classification, or the like, to identify naturally occurring patterns in the training data. As an example, the training data may be clustered into groups based on identified similarities and/or patterns. K-means clustering or K-Nearest Neighbors may also be used, which may be supervised or unsupervised. Combinations of K-Nearest Neighbors and an unsupervised cluster technique may also be used. For semi-supervised learning, a combination of training data with pre-assigned labels or scores and training data without pre-assigned labels or scores may be used to train the model.

When reinforcement learning is employed, an agent (e.g., an algorithm) may be trained to make a decision from the training data through trial and error. For example, based on making a decision, the agent may then receive feedback (e.g., a positive reward if the prediction was above a predetermined threshold), adjust its next decision to maximize the reward, and repeat until a loss function is optimized.

After being trained, the trained model may be stored and subsequently applied by the ultrasound system 110 during the deployment phase. For example, during the deployment phase, the trained model executed by the ultrasound system 110 may receive input data. During the deployment phase, the trained model may perform one or more operations as described in connection with FIG. 4.

After being deployed, the trained model may be monitored during the monitoring phase. For example, during the monitoring phase, the model may generate monitoring data that is used to monitor the trained model. The monitoring data may include data that identifies an output as determined by an operator. During the monitoring phase, monitoring data may be analyzed along with the predicted output data and input data to determine an accuracy of the trained model. According to an embodiment, based on the analysis, the process may return to the training phase, where values of one or more variables of the model may be adjusted to improve the accuracy of the model.

As further shown in FIG. 6, the process 600 may include determining a measurement location for spectral Doppler data acquisition based on the position of the regurgitant jet (operation 630). For example, the ultrasound system 110 may determine a measurement location for spectral Doppler data acquisition based on the position of the regurgitant jet.

According to an embodiment, the ultrasound system 110 may determine a CW line for CW Doppler ultrasound data acquisition based on the measurement location corresponding to the position of the regurgitant jet. The ultrasound system 110 may determine measurement location position information of the measurement location. The measurement point position information may identify a position of the measurement point in a coordinate space of the ultrasound system 110. For example, the ultrasound system 110 may determine a 3D coordinate of the measurement location based on tracking data of the ultrasound probe 202 acquired by the tracking system 120. The ultrasound system 110 may determine ultrasound probe position information of the ultrasound probe 202. The ultrasound probe position information may identify a position of the ultrasound probe 202 in the coordinate space of the ultrasound system 110. For example, the ultrasound system 110 may determine a 3D coordinate of the ultrasound probe 202 based on tracking data of the ultrasound probe 202 acquired by the tracking system 120. The ultrasound system 110 may determine a CW line based on the measurement location position information of the measurement location and the ultrasound probe position information of the ultrasound probe 202. For example, the ultrasound system 110 may determine a CW line that coincides with the 3D coordinate of the measurement point and the 3D coordinate of the ultrasound probe 202. The ultrasound system 110 may determine an azimuth, a tilt, and an elevation of the CW line.

According to an embodiment, the ultrasound system 110 may determine a PW line for PW Doppler ultrasound data acquisition based on the measurement location corresponding to the position of the regurgitant jet. The ultrasound system 110 may determine measurement location position information of the measurement location. The measurement point position information may identify a position of the measurement point in a coordinate space of the ultrasound system 110. For example, the ultrasound system 110 may determine a 3D coordinate of the measurement location based on tracking data of the ultrasound probe 202 acquired by the tracking system 120. The ultrasound system 110 may determine ultrasound probe position information of the ultrasound probe 202. The ultrasound probe position information may identify a position of the ultrasound probe 202 in the coordinate space of the ultrasound system 110. For example, the ultrasound system 110 may determine a 3D coordinate of the ultrasound probe 202 based on tracking data of the ultrasound probe 202 acquired by the tracking system 120. The ultrasound system 110 may determine a PW line based on the measurement location position information of the measurement location and the ultrasound probe position information of the ultrasound probe 202. For example, the ultrasound system 110 may determine a PW line that coincides with the 3D coordinate of the measurement point and the 3D coordinate of the ultrasound probe 202. The ultrasound system 110 may determine an azimuth, a tilt, and an elevation of the PW line.

According to an embodiment, the ultrasound system 110 may determine a PW gate for PW Doppler ultrasound data acquisition. The PW gate may be a segment along the PW line. The PW gate may also be referred to as a "PW sample." The ultrasound system 110 may determine the PW gate using a predetermined configuration for the PW gate. For example, the predetermined configuration may define a length of the PW gate, may define a length proximal to the measurement position, may define a length distal to the measurement location, or the like. Alternatively, the ultrasound system 110 may determine the PW gate based on a characteristic of the structure of interest in the ROI. For example, the ultrasound system 110 may determine the PW gate based on size of the structure of interest, based on a location of the structure of interest, or the like.

As further shown in FIG. 6, the process 600 may include acquiring spectral Doppler ultrasound data corresponding to the measurement location (operation 640). For example, the ultrasound system may automatically acquire spectral Doppler ultrasound data corresponding to the measurement location based on the measurement location of the determined regurgitant jet.

According to an embodiment, the ultrasound system 110 may acquire the spectral Doppler data based on determining the CW line that coincides with the position of the regurgitant jet. For example, the ultrasound system 110 may control the ultrasound probe 202 to acquire CW Doppler ultrasound data along the CW line. According to another embodiment, the ultrasound system 110 may acquire the spectral Doppler data based on determining the PW line and the PW gate that coincide with the regurgitant jet. For example, the ultrasound system 110 may control the ultrasound probe 202 to acquire PW Doppler ultrasound data along the PW line and within the PW gate.

As further shown in FIG. 6, the process 600 may include displaying spectral Doppler information corresponding to the spectral Doppler ultrasound data (operation 650). For example, the ultrasound system may display spectral Doppler information corresponding to the spectral Doppler ultrasound data in a similar manner as described above in connection with operation 440 of FIG. 4.

Although FIG. 6 depicts a particular set of operations, it should be understood that other embodiments may include different operations, such as more operations, less operations, or the like. Further, although FIG. 6 depicts a particular sequence of operations, it should be understood that other embodiments may include a different sequence of operations. Further still, one or more operations may be performed simultaneously, concurrently, etc.

Figure 7:
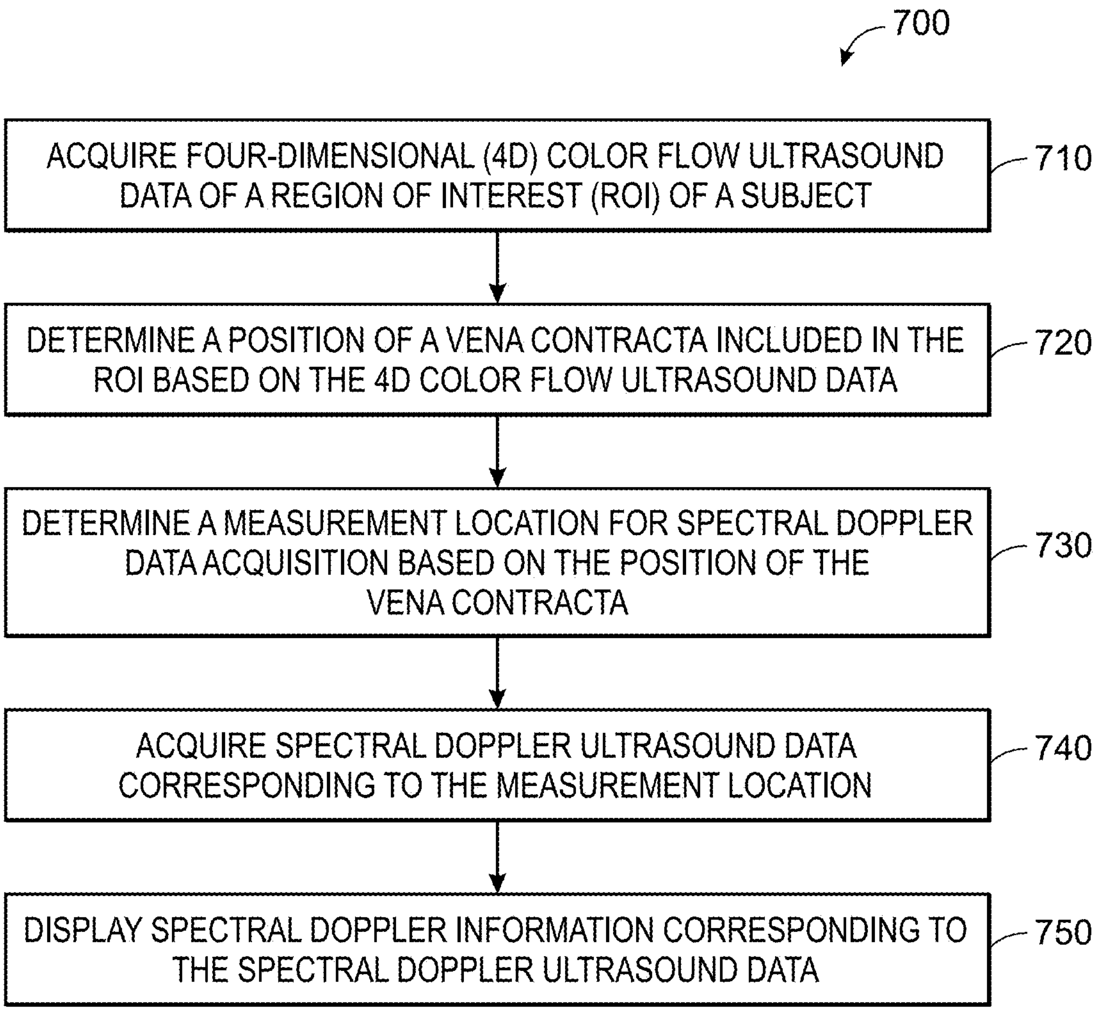
FIG. 7 is a flowchart of an example process for automatic spectral Doppler ultrasound data acquisition based on a determined position of a *vena contracta.*

FIG. 7 is a flowchart of an example process 700 for automatic spectral Doppler ultrasound data acquisition based on a determined position of a *vena contracta*. According to an embodiment, one or more operations of FIG. 7 may be performed by the processor 216. Additionally, or alternatively, one or more operations of FIG. 4 may be performed by another component, or set of components, of the ultrasound system 110, such as the ultrasound probe 202, the transmit beamformer 204, the transmitter 206, the elements 208, the receiver 210, the receive beamformer 212, the user input device 214, the display 218, the memory 220, and/or the communication interface 222.

As shown in FIG. 7, the process 700 may include acquiring four-dimensional (4D) color flow ultrasound data of a region of interest (ROI) of a subject (operation 710). For example, the ultrasound system 110 may acquire 4D color flow ultrasound data of an ROI of a subject in a similar manner as described above in connection with operation 410 of FIG. 4.

As further shown in FIG. 7, the process 700 may include determining a position of a *vena contracta* included in the ROI based on the 4D color flow ultrasound data (operation 720). For example, the ultrasound 110 may determine a position of a *vena contracta* in the ROI based on the 4D color flow ultrasound data.

According to an embodiment, the ultrasound system 110 may automatically determine the position of the *vena contracta* using an image processing technique, an AI model, or the like, in a similar manner as described above with connection to FIG. 6.

Alternatively, the ultrasound system 110 may determine the position of the *vena contracta* based on a user input. For example, the user may interact with the user input device 214 to select a location of the *vena contracta*. As an example, the user may place intersecting lines to select the location of the *vena contracta*. Alternatively, the user may encircle the *vena contracta* using a free-form selection.

According to an embodiment, the ultrasound system 110 may determine a user input selecting a measurement location in the 4D color flow ultrasound image of the ROI of the subject based on the *vena contracta*. In this way, the ultrasound system 101 may use the *vena contracta* area and the CW velocity time integral to automatically determine a regurgitant volume.

As further shown in FIG. 7, the process 700 may include determining a measurement location for spectral Doppler data acquisition based on the position of the *vena contracta* (operation 730). For example, the ultrasound system 110 may determine a measurement location for spectral Doppler data acquisition based on the position of the *vena contracta*.

According to an embodiment, the ultrasound system 110 may determine a CW line for CW Doppler ultrasound data acquisition based on the measurement location corresponding to the position of the *vena contracta*. The ultrasound system 110 may determine measurement location position information of the measurement location. The measurement point position information may identify a position of the measurement point in a coordinate space of the ultrasound system 110. For example, the ultrasound system 110 may determine a 3D coordinate of the measurement location based on tracking data of the ultrasound probe 202 acquired by the tracking system 120. The ultrasound system 110 may determine ultrasound probe position information of the ultrasound probe 202. The ultrasound probe position information may identify a position of the ultrasound probe 202 in the coordinate space of the ultrasound system 110. For example, the ultrasound system 110 may determine a 3D coordinate of the ultrasound probe 202 based on tracking data of the ultrasound probe 202 acquired by the tracking system 120. The ultrasound system 110 may determine a CW line based on the measurement location position information of the measurement location and the ultrasound probe position information of the ultrasound probe 202. For example, the ultrasound system 110 may determine a CW line that coincides with the 3D coordinate of the measurement point and the 3D coordinate of the ultrasound probe 202. The ultrasound system 110 may determine an azimuth, a tilt, and an elevation of the CW line.

According to an embodiment, the ultrasound system 110 may determine a PW line for PW Doppler ultrasound data acquisition based on the measurement location corresponding to the position of the *vena contracta*. The ultrasound system 110 may determine measurement location position information of the measurement location. The measurement point position information may identify a position of the measurement point in a coordinate space of the ultrasound system 110. For example, the ultrasound system 110 may determine a 3D coordinate of the measurement location based on tracking data of the ultrasound probe 202 acquired by the tracking system 120. The ultrasound system 110 may determine ultrasound probe position information of the ultrasound probe 202. The ultrasound probe position information may identify a position of the ultrasound probe 202 in the coordinate space of the ultrasound system 110. For example, the ultrasound system 110 may determine a 3D coordinate of the ultrasound probe 202 based on tracking data of the ultrasound probe 202 acquired by the tracking system 120. The ultrasound system 110 may determine a PW line based on the measurement location position information of the measurement location and the ultrasound probe position information of the ultrasound probe 202. For example, the ultrasound system 110 may determine a PW line that coincides with the 3D coordinate of the measurement point and the 3D coordinate of the ultrasound probe 202. The ultrasound system 110 may determine an azimuth, a tilt, and an elevation of the PW line.

According to an embodiment, the ultrasound system 110 may determine a PW gate for PW Doppler ultrasound data acquisition. The PW gate may be a segment along the PW line. The PW gate may also be referred to as a "PW sample." The ultrasound system 110 may determine the PW gate using a predetermined configuration for the PW gate. For example, the predetermined configuration may define a length of the PW gate, may define a length proximal to the measurement position, may define a length distal to the measurement location, or the like. Alternatively, the ultrasound system 110 may determine the PW gate based on a characteristic of the structure of interest in the ROI. For example, the ultrasound system 110 may determine the PW gate based on size of the structure of interest, based on a location of the structure of interest, or the like.

As further shown in FIG. 7, the process 700 may include acquiring spectral Doppler ultrasound data corresponding to the measurement location (operation 740). For example, the ultrasound system 110 may automatically acquire spectral Doppler ultrasound data corresponding to the measurement location based on the measurement location of the determined regurgitant jet.

According to an embodiment, the ultrasound system 110 may acquire the spectral Doppler data based on determining the CW line that coincides with the position of the *vena contracta*. For example, the ultrasound system 110 may control the ultrasound probe 202 to acquire CW Doppler ultrasound data along the CW line. According to another embodiment, the ultrasound system 110 may acquire the spectral Doppler data based on determining the PW line and the PW gate that coincide with the regurgitant jet. For example, the ultrasound system 110 may control the ultrasound probe 202 to acquire PW Doppler ultrasound data along the PW line and within the PW gate.

As further shown in FIG. 7, the process 700 may include displaying spectral Doppler information corresponding to the spectral Doppler ultrasound data (operation 750). For example, the ultrasound system may display spectral Doppler information corresponding to the spectral Doppler ultrasound data in a similar manner as described above in connection with operation 440 of FIG. 4.

Although FIG. 7 depicts a particular set of operations, it should be understood that other embodiments may include different operations, such as more operations, less operations, or the like. Further, although FIG. 7 depicts a particular sequence of operations, it should be understood that other embodiments may include a different sequence of operations. Further still, one or more operations may be performed simultaneously, concurrently, etc.

Figure 8:
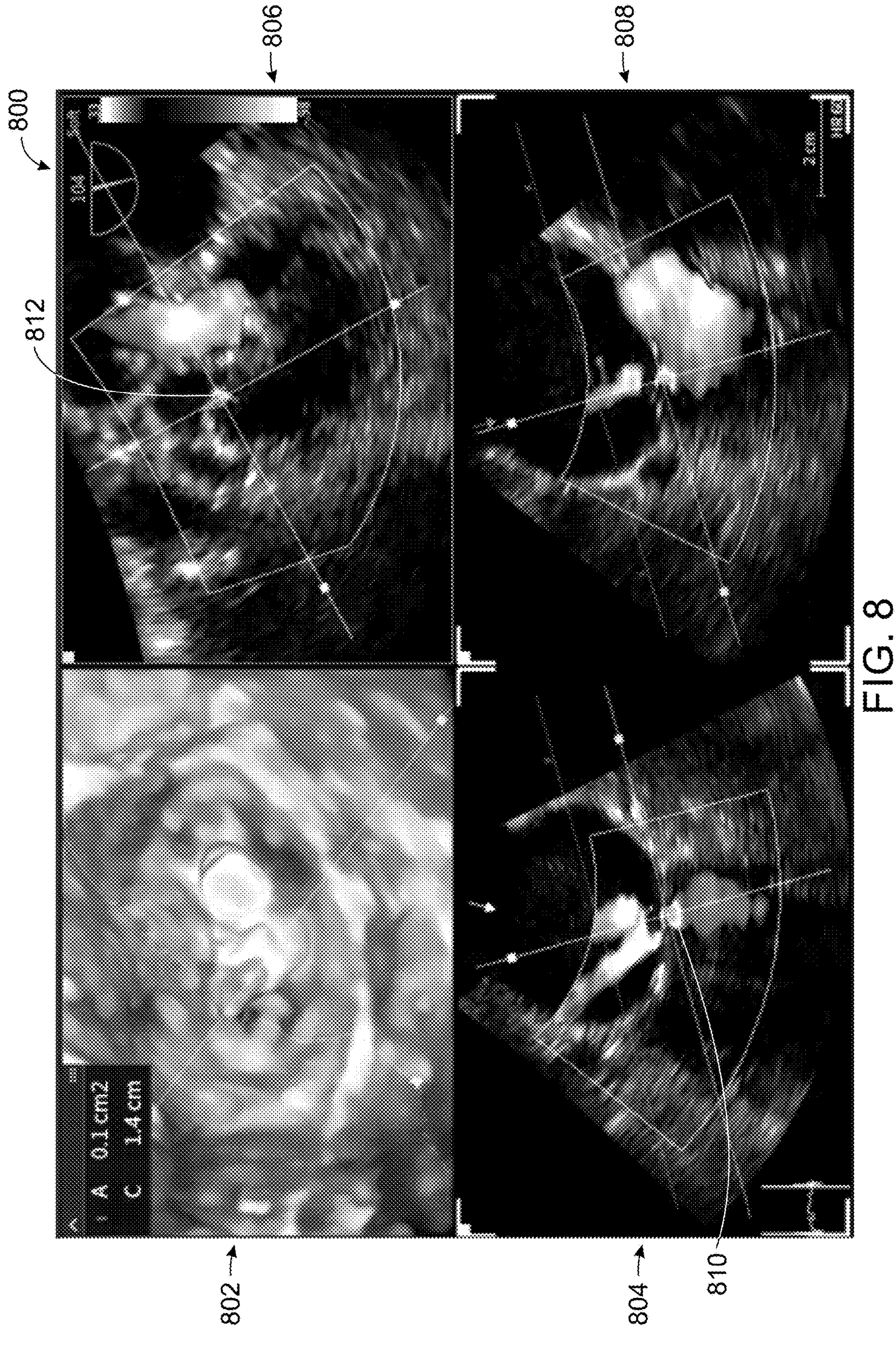
FIG. 8 is a diagram of an example process for automatic spectral Doppler ultrasound data acquisition based on a determined position of a *vena contracta.*

FIG. 8 is a diagram of an example process 800 for automatic spectral Doppler ultrasound data acquisition based on a determined position of a *vena contracta*.

As shown in FIG. 8, the ultrasound system 110 may display a 4D color flow ultrasound image 802 depicting a regurgitant jet, a first 2D slice 804 of the 4D color flow ultrasound image 802, a second 2D slice 806 of the 4D color flow ultrasound image 802, and a third 2D slice 808 of the 4D color flow ultrasound image 802. As shown in FIG. 8 by reference number 810, the user may interact with the first 2D slice 804 to align measurement lines with respect to the *vena contracta* of the regurgitant jet. Further, as shown in FIG. 8 by reference number 812, the user may encircle the *vena contracta* in the second 2D slice 806 to measure the diameter of the *vena contracta*. The ultrasound system 110 may acquire spectral Doppler ultrasound data corresponding to the position of the *vena contracta*, and determine spectral Doppler information corresponding to the spectral Doppler ultrasound data. For example, the ultrasound system 110 may determine a regurgitant volume based on the spectral Doppler information and the measurement of the *vena contracta*.

Although embodiments herein describe the assessment of mitral valve regurgitation, it should be understood that the embodiments herein are applicable to assessing other types of fluid flow in various anatomical regions of a subject.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound system comprising:
- a memory configured to store instructions; and
- one or more processors configured to execute the instructions to:
  - acquire, via an ultrasound probe, four-dimensional (4D) color flow ultrasound data of a region of interest (ROI) of a subject;
  - display a 4D color flow ultrasound image of the ROI of the subject based on the 4D color flow ultrasound data;
  - receive a user input selecting a measurement location in the 4D color flow ultrasound image of the ROI of the subject;
  - determine a first position of the measurement location in a coordinate space of the ultrasound system;
  - determine a second position of the ultrasound probe in the coordinate space of the ultrasound system;
  - automatically acquire, via the ultrasound probe, spectral Doppler ultrasound data corresponding to the measurement location based on the user input using the first position and the second position; and
  - display spectral Doppler information corresponding to the spectral Doppler ultrasound data.

2. The ultrasound system of claim 1, wherein the spectral Doppler ultrasound data is continuous wave (CW) Doppler ultrasound data or pulsed wave (PW) ultrasound data.

3. The ultrasound system of claim 2, wherein the one or more processors are further configured to:
- determine a CW line for CW Doppler ultrasound data acquisition that coincides with the first position and the second position.

4. The ultrasound system of claim 2, wherein the one or more processors are further configured to:
- determine a PW line for PW Doppler ultrasound data acquisition that coincides with the first position and the second position.

5. The ultrasound system of claim 1, wherein the first position is a first three-dimensional (3D) coordinate, and wherein the second position is a second 3D coordinate.

6. The ultrasound system of claim 1, wherein the one or more processors are configured to receive the user input selecting the measurement location in the 4D color flow ultrasound image of the ROI of the subject on a volume rendering or on a two-dimensional (2D) slice of the color flow ultrasound data.

7. The ultrasound system of claim 2, wherein the one or more processors are further configured to:
determine an azimuth, a tilt, and an elevation of a CW line or a PW line using the first position and the second position.

8. A method comprising:
acquiring, via an ultrasound probe of an ultrasound system, four-dimensional (4D) color flow ultrasound data of a region of interest (ROI) of a subject;
displaying a 4D color flow ultrasound image of the ROI of the subject based on the 4D color flow ultrasound data;
receiving a user input selecting a measurement location in the 4D color flow ultrasound image of the ROI of the subject;
determining a first position of the measurement location in a coordinate space of the ultrasound system;
determining a second position of the ultrasound probe in the coordinate space of the ultrasound system;
automatically acquiring, via the ultrasound probe, spectral Doppler ultrasound data corresponding to the measurement location based on the user input using the first position and the second position; and
displaying spectral Doppler information corresponding to the spectral Doppler ultrasound data.

9. The method of claim 8, wherein the spectral Doppler ultrasound data is continuous wave (CW) Doppler ultrasound data or pulsed wave (PW) ultrasound data.

10. The method of claim 9, further comprising:
determining a CW line for CW Doppler ultrasound data acquisition that coincides with the first position and the second position.

11. The method of claim 9, further comprising:
determining a PW line for PW Doppler ultrasound data acquisition based on the measurement location that coincides with the first position and the second position.

12. The method of claim 11, further comprising:
determining a PW gate for the PW Doppler ultrasound data acquisition based on the measurement location.

13. The method of claim 8, wherein the first position is a first three-dimensional (3D) coordinate, and wherein the second position is a second 3D coordinate.

14. The method of claim 8, wherein the determining the user input comprises determining the user input selecting the measurement location in the 4D color flow ultrasound image of the ROI of the subject based on a *vena contracta*.

15. A non-transitory computer-readable medium storing instructions that, when executed by one or more processors of an ultrasound system, cause the one or more processors to:
acquire, via an ultrasound probe, four-dimensional (4D) color flow ultrasound data of a region of interest (ROI) of a subject;
display a 4D color flow ultrasound image of the ROI of the subject based on the 4D color flow ultrasound data;
receive a user input selecting a measurement location in the 4D color flow ultrasound image of the ROI of the subject;
determine a first position of the measurement location in a coordinate space of the ultrasound system;
determine a second position of the ultrasound probe in the coordinate space of the ultrasound system;
automatically acquire, via the ultrasound probe, spectral Doppler ultrasound data corresponding to the measurement location based on the user input using the first position and the second position; and
display spectral Doppler information corresponding to the spectral Doppler ultrasound data.

16. The non-transitory computer-readable medium of claim 15, wherein the spectral Doppler ultrasound data is continuous wave (CW) Doppler ultrasound data or pulsed wave (PW) ultrasound data.

17. The non-transitory computer-readable medium of claim 16, wherein the instructions further cause the one or more processors to:
determine a CW line for CW Doppler ultrasound data acquisition that coincides with the first position and the second position.

18. The non-transitory computer-readable medium of claim 16, wherein the instructions further cause the one or more processors to:
determine a PW line for PW Doppler ultrasound data acquisition that coincides with the first position and the second position.

19. The non-transitory computer-readable medium of claim 18, wherein the instructions further cause the one or more processors to:
determine a PW gate for the PW Doppler ultrasound data acquisition based on the measurement location.

20. The non-transitory computer-readable medium of claim 15, wherein the first position is a first three-dimensional (3D) coordinate, and wherein the second position is a second 3D coordinate.

* * * * *